(12) United States Patent
Hagg

(10) Patent No.: US 9,895,575 B2
(45) Date of Patent: Feb. 20, 2018

(54) DEVICE FOR TRAINING OF FACE, LIP AND THROAT MUSCLES

(71) Applicant: MYOROFACE AB, Hudiksvall (SE)

(72) Inventor: Mary Hagg, Forsa (SE)

(73) Assignee: MYOROFACE AB, Hudicksvall (SE)

( * ) Notice: Subject to any disclaimer, the term of this patent is extended or adjusted under 35 U.S.C. 154(b) by 80 days.

(21) Appl. No.: 14/777,020

(22) PCT Filed: Mar. 10, 2014

(86) PCT No.: PCT/SE2014/050287
§ 371 (c)(1),
(2) Date: Sep. 15, 2015

(87) PCT Pub. No.: WO2014/142735
PCT Pub. Date: Sep. 18, 2014

(65) Prior Publication Data
US 2016/0030802 A1 Feb. 4, 2016

(30) Foreign Application Priority Data

Mar. 15, 2013 (SE) ........................................ 1350314

(51) Int. Cl.
*A63B 23/03* (2006.01)
*A61H 7/00* (2006.01)
(Continued)

(52) U.S. Cl.
CPC ............ *A63B 23/032* (2013.01); *A61B 5/224* (2013.01); *A61B 5/4205* (2013.01); *A61B 5/682* (2013.01);
(Continued)

(58) Field of Classification Search
CPC . A61C 19/06; A63B 23/032; A63B 21/00185; A61B 5/224; A61B 5/4205;
(Continued)

(56) References Cited

U.S. PATENT DOCUMENTS 3,744,485 A 7/1973 Worthy
3,805,771 A 4/1974 Wright
(Continued)

FOREIGN PATENT DOCUMENTS

DE 9001001 U1 4/1990
DE 3915505 11/1990
(Continued)

OTHER PUBLICATIONS

Extended European Search Report dated Oct. 12, 2016; Application No. 14762798.8.
(Continued)

*Primary Examiner* — Andrews S Lo
(74) *Attorney, Agent, or Firm* — Young & Thompson

(57) ABSTRACT

A device for therapeutic includes a rigid screen (1) that is insertable behind the upper and lower lips of a user's mouth, the screen having a compound curvature and in a horizontal plane generally U-shaped profile, and in a vertical plane a convexo-concave cross-sectional profile that is gradually flattening from a central mid region towards the left and right ends (12, 13) thereof, the ends extended to reach at least past the premolar teeth on each side in the upper and lower jaws of the user when applied. A handle is attached to extend forward from a central mid region in the convex front face of the screen, the handle including a rigid stem (2) projecting from the front face at a neutral angle with respect to upper (5) and lower (6) halves of the screen (1), diverging from the stem in the vertical view.

16 Claims, 2 Drawing Sheets

(51) Int. Cl.
*A61H 21/00* (2006.01)
*A61B 5/00* (2006.01)
*A61B 5/22* (2006.01)
*A63B 21/00* (2006.01)

(52) U.S. Cl.
CPC .............. *A61H 7/001* (2013.01); *A61H 21/00* (2013.01); *A61H 2201/0153* (2013.01); *A61H 2201/1253* (2013.01); *A61H 2201/1604* (2013.01); *A61H 2201/1695* (2013.01); *A61H 2201/5071* (2013.01); *A61H 2205/02* (2013.01); *A63B 21/00185* (2013.01)

(58) Field of Classification Search
CPC ........ A61B 5/682; A61H 7/001; A61H 21/00; A61H 2201/0153; A61H 2201/1253; A61H 2201/1604; A61H 2201/1695; A61H 2201/5071; A61H 2205/02; A61J 17/001; A61J 11/007; A61J 17/02; A61J 17/00
USPC ..... 482/148, 11, 10; 606/234, 236; D24/194
See application file for complete search history.

(56) References Cited

U.S. PATENT DOCUMENTS

| | | | |
|---|---|---|---|
| 5,165,423 A | 11/1992 | Fowler et al. | |
| 5,624,257 A | 4/1997 | Farrell | |
| 5,732,715 A * | 3/1998 | Jacobs | A63B 71/085 128/861 |
| 5,921,240 A | 7/1999 | Gall | |
| 6,076,526 A | 6/2000 | Abdelmessih | |
| 6,263,877 B1 | 7/2001 | Gall | |
| 6,412,489 B1 | 7/2002 | Sue | |
| 6,514,176 B1 * | 2/2003 | Norton | A63B 21/002 128/848 |
| 6,935,857 B1 * | 8/2005 | Farrell | A61C 7/08 128/861 |
| D659,253 S * | 5/2012 | Valderrama | D24/194 |
| D754,865 S * | 4/2016 | Hagg | D24/200 |
| 2003/0089371 A1 | 5/2003 | Robertson et al. | |
| 2003/0111083 A1 | 6/2003 | Bancroft | |
| 2003/0232699 A1* | 12/2003 | Norton | A63B 21/002 482/11 |
| 2004/0234929 A1* | 11/2004 | Fischer | A61C 5/00 433/215 |
| 2005/0192157 A1* | 9/2005 | Norton | A63B 21/002 482/11 |
| 2007/0027478 A1* | 2/2007 | Tesini | A61J 17/00 606/234 |
| 2008/0046011 A1* | 2/2008 | Brown | A61J 17/001 606/236 |
| 2012/0265244 A1* | 10/2012 | Valderrama | A61L 2/07 606/234 |
| 2013/0177867 A1* | 7/2013 | Morales | A61C 19/063 433/48 |
| 2013/0247922 A1* | 9/2013 | Kamradt | A63B 71/085 128/862 |
| 2014/0100498 A1 | 4/2014 | Richter | |
| 2014/0246028 A1* | 9/2014 | Wilson | A63B 71/085 128/861 |
| 2016/0128816 A1* | 5/2016 | Khangura | A61C 19/066 433/29 |

FOREIGN PATENT DOCUMENTS

| | | |
|---|---|---|
| DE | 202012103831 U1 | 12/2012 |
| JP | 2007117688 A | 5/2007 |
| JP | 2007319304 A | 12/2007 |
| JP | 2008237276 | 10/2008 |
| WO | 9802119 | 1/1998 |
| WO | 2012031702 A2 | 3/2012 |

OTHER PUBLICATIONS

International Search Report, dated Jun. 30, 2014, from corresponding PCT application.

* cited by examiner

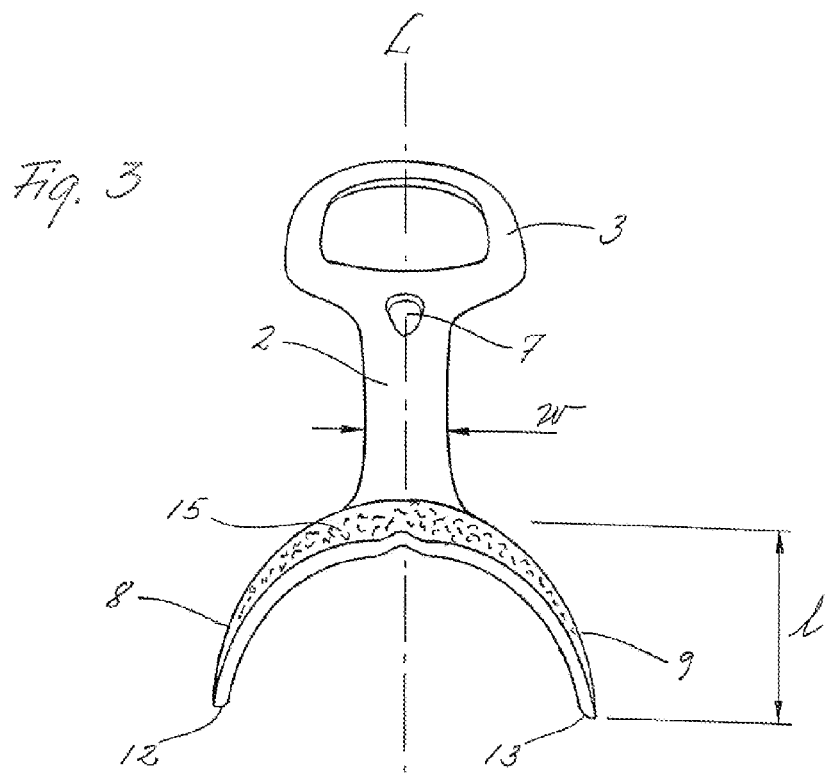
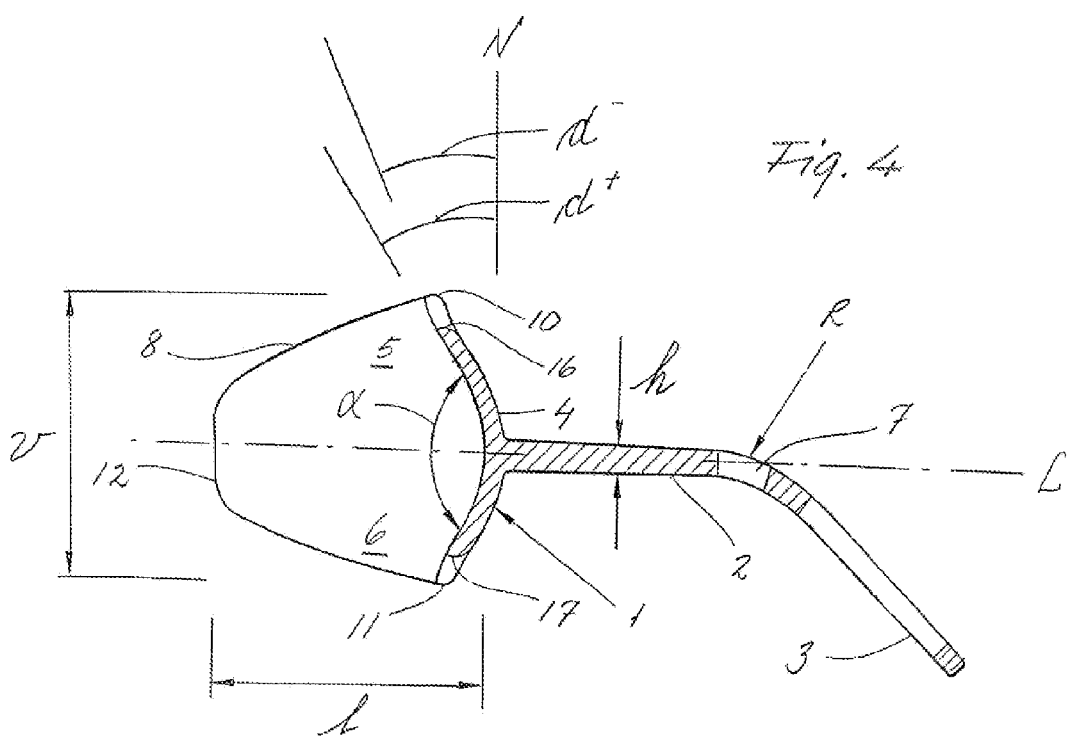

DEVICE FOR TRAINING OF FACE, LIP AND THROAT MUSCLES

TECHNICAL FIELD OF THE INVENTION

The present invention relates to devices for therapeutic use, and more specifically relates to an oral screen that is useful in training for recovery and improvement of muscular functions in, inter alia, face, mouth and throat.

BACKGROUND AND PRIOR ART

It has been shown in studies that lip muscle training can improve swallowing capacity in stroke patients (see: Hägg Mary, and Anniko Matti, 2008 "Lip muscle training in stroke patients with dysphagia", Acta Oto-Laryngologica, 128:9, 1027-1033; 2010 "Influence of lip force on swallowing capacity in stroke patients and in healthy subjects", Acta Oto-Laryngologica 130: 1204-8, and: Hagg Mary, Tibbling Lita 2013 "Longstanding effect and outcome differences of palatal plate and oral screen training on stroke related dysphagia", The Open Rehabilitation Journal, 2013, 6, 26-33.

Indeed, training with an oral screen which is insertable into the mouth pre-dentally behind closed lips and to which a tension load is applied is effective for stimulation and activation not only of lip muscles, but affects also other muscles in the entire orofacial complex and in the upper third of esophagus, in stomach via the sensory cranial nerve vagus, and in addition effects improvement of gross motor skills in humans. It can also be effective in order to recover and improve impaired muscle functions resulting from neurological diseases other than stroke, orofacial cancer, chromosomal abnormalities, and accidental trauma or from natural causes, such as ageing, e.g.

An exercising device for the lip and cheek area is previously disclosed in U.S. Pat. No. 3,744,485. This device is adapted to be introduced into the mouth and fitted in the space defined by the user's teeth and inner lip area immediately adjacent the mouth. The device comprises a handle and a U-shaped flange connected thereto wherein this flange fits in the aforementioned area whereupon with the mouth closed over the flange and the handle extending outwardly there from, inward and outward motion may be imparted to the device.

A device designed for exercise of lip muscles is previously known from German Utility Model Registration No. 90 01 001. This device comprises a mouthpiece designed for insertion behind the lips of the user, and a handle connected to the front of the mouthpiece via an elongate, wire-shaped bar by which a tensioning force can be applied to the mouthpiece. The mouthpiece has a convex front side facing the lips and a concave rear side facing the teeth.

The mouthpiece disclosed in DE 90 01 001 is basically intended for strengthening the lip muscles with users having special demands for strong and elastic lips such as speakers, singers and players of brass and wood wind instruments.

The disclosures of U.S. Pat. No. 3,744,485 and DE 90 01 001 however contain little advice to a skilled person who is searching for an ergonomic and efficient lip and face muscle trainer that effects sensorimotor stimulation of larger groups of muscles in patients with pathologically impaired muscle functions in face, mouth and throat.

SUMMARY OF THE INVENTION

The present invention therefore aims at providing a device which in use provides improved sensorimotor stimulation of lips, and potentially of the entire orofacial complex (lip, face and throat muscles).

The object is met in a device insertable behind the upper and lower lips of a user's mouth, the device comprising a rigid screen having a compound curvature and in a horizontal plane generally U-shaped profile, the screen in a vertical plane having a convexo-concave cross-sectional profile that is gradually flattening from a central mid region towards left and right ends thereof, the ends extended to reach at least past the premolar teeth on each side in upper and lower jaws of the user as applied. A handle is further arranged to extend forward from a central mid region in the convex front face of the screen, the handle comprising a rigid stem projecting from the front face at a neutral angle with respect to upper and lower halves of the screen, diverging from the stem in the vertical view.

The compound curvature of the screen not only ensures a comfortable application of the screen in the mouth of a user, but also permits maximizing the screen's dimensions in order to involve and stimulate more nerves and muscles in the mouth and cheeks.

Tests performed on patients indicate that training with an oral screen having the compound curvature and lateral extension as claimed, under supervision from trained personnel, can in fact stimulate the entire natural neuromuscular chain activity including muscles and cranial nerves in the orofacial complex, from the lips down to the stomach, in a natural way which is similar to that which initiates a swallowing act.

In particular, the prescribed extension of the screen past the premolar teeth on each side of the mouth ensures efficient stimulation of the buccinator muscle and buccinator mechanism which is of importance for the swallowing capacity (as used in this context, a person's swallowing capacity involves the coordinated activation of the m. orbicularis oris, m. buccinator, m. constrictor pharyngeus superior).

The sensorimotor stimulation can be even further improved when, as in a preferred embodiment, a friction enhancing texture is applied onto the front face of the oral screen.

The texture can be realized in the form of a regular or irregular pattern of ridges or grooves running in parallel or intersecting each other, or in the form of small cavities or projections or combinations thereof. In a preferred embodiment the texture is realized as a coarse surface structure that is imprinted on the front face of the screen during molding thereof, or resulting from abrasive blasting of the front face after molding.

The oral screen of the present invention is advantageously and preferably formed in one piece by molding in a plastic material, such as acrylic plastic, e.g. Metal or other plastic material can alternatively be used for producing the oral screen.

It is further preferred that the stem which projects from the front face is a flat geometry with its major dimension being horizontal. In particular, the horizontal width of the stem transverse to its longitudinal dimension is important not only to provide structural stability and strength to the device: the horizontal dimension of the stem also provides a lip contact area which is increased in comparison to prior art as the stem protrudes between the closed lips in use of the oral screen. The lip contact with the stem is considered important during training since it helps the user to position the device correctly and aids in muscle control and activation of the entire buccinator mechanism.

The purpose of the stem is to transfer a tension load that can be manually applied via a grip which is attached in the free end of the stem pointing away from the front face of the screen. The grip can be formed as an eye suitable for insertion of a user's finger or thumb and yet sufficiently sized to offer grasping by the hand of the user.

In a region where the grip attaches to the stem the grip may be angled out of direction of the stem to provide access to a lug that is formed in said region and intended for attachment of a measurement instrument which is to be operated in the longitudinal direction of the stem. The prime purpose of attaching a measurement instrument will be to determine the status of the user and to follow-up training and change in status. The lug may additionally be used for applying a controlled tension load via the measurement instrument or via other controllable tension spring.

In order to provide contact for maximum sensorimotor stimulation of lips and cheek, the upper and lower halves of the screen are dimensioned to substantially cover the vertical distance between the transition regions that connect the upper and lower lips to the appertaining gum, respectively. To this purpose, an upper recess and an opposite lower recesses is formed in the upper and lower edges of the screen, the recesses having a V-shape adapted for accommodation of the upper and lower lugs of skin, or lip bands, which attach to the lip and gum.

As understood from the above, the invention teaches that in applied position the oral screen occupies substantially all vertical space between the lips and the gums when the lips are closed about the stem. This extensive coverage can be accomplished by carefully determining the curvature and the vertical cross-sectional profile of the oral screen, which is of a critical nature in order to avoid uncomfortable stress in the tissue that connects the lip to the gum. In a preferred embodiment the oral screen is designed with a cross-sectional profile in the vertical plane that encloses an intermediate vertical angle between the diverging upper and lower screen halves which amounts to the order of 120-140°. In a currently highly preferred embodiment the intermediate angle is about 130° on average, or ranging from approximately 120° at a vertical mid region where the screen halves meet to approximately 140° or less at the upper and lower edges, in a slightly S-curved sectional profile of the oral screen.

Notably, clinical test has shown that training with an oral screen designed as disclosed herein will have beneficial effects also in the treatment of patients with swallowing problems/dysphagia at the oral, pharyngeal, and esophageal level. This is considered to be attributed to the fact that stressing of the lip muscles with a tensioning load starts a chain of neuromuscular activity in the mouth, the pharynx and upper part of the gullet or esophagus, an activity which is the same as that which initiates an act of swallowing. In particular, the oral screen with enhanced sensorimotor stimulation effect as provided for in the present invention will in use stimulate and initiate a coordinated activation of facial muscles which are involved in lip closure and in creation of a negative pressure in the mouth cavity, muscles involved in closure of the nasopharyngeal area and in preparing the swallowing act, all of which are associated with the facial nerve and the buccinator mechanism.

Beside the positive effect on the swallowing ability, training with the oral screen may additionally have effect to reduce snoring or drooling, or to improve the ability of facial expressions, improve speech and to recreate symmetry in the face after trauma, e.g. These and other advantages are accomplished through the oral screen of the present invention, the characterizing features of which are presented in more detail below.

SHORT DESCRIPTION OF THE DRAWINGS

An embodiment of the invention will now be described in detail with reference made to the appended schematic drawings. In the drawings, FIG. 1 is a perspective view of the oral screen of the present invention;

FIG. 3 is a view from above, and

FIG. 4 is a cross-sectional view and vertical projection in a vertical plane through the central mid-portion of the oral screen depicted in FIGS. 1 to 3.

DETAILED DESCRIPTION OF A PREFERRED EMBODIMENT

Figure 1:
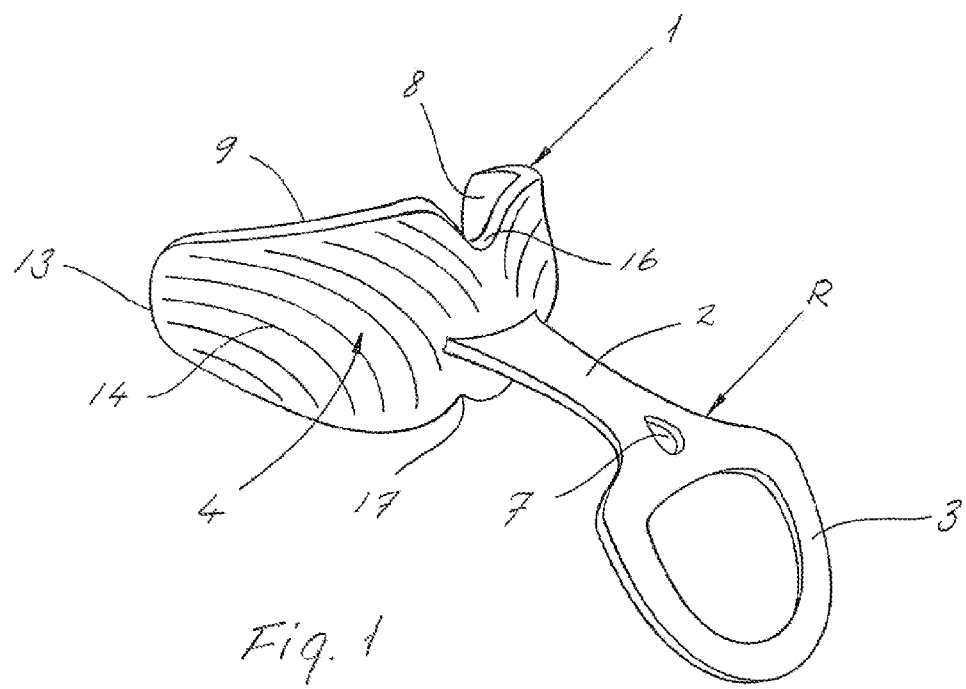
Figure 2:
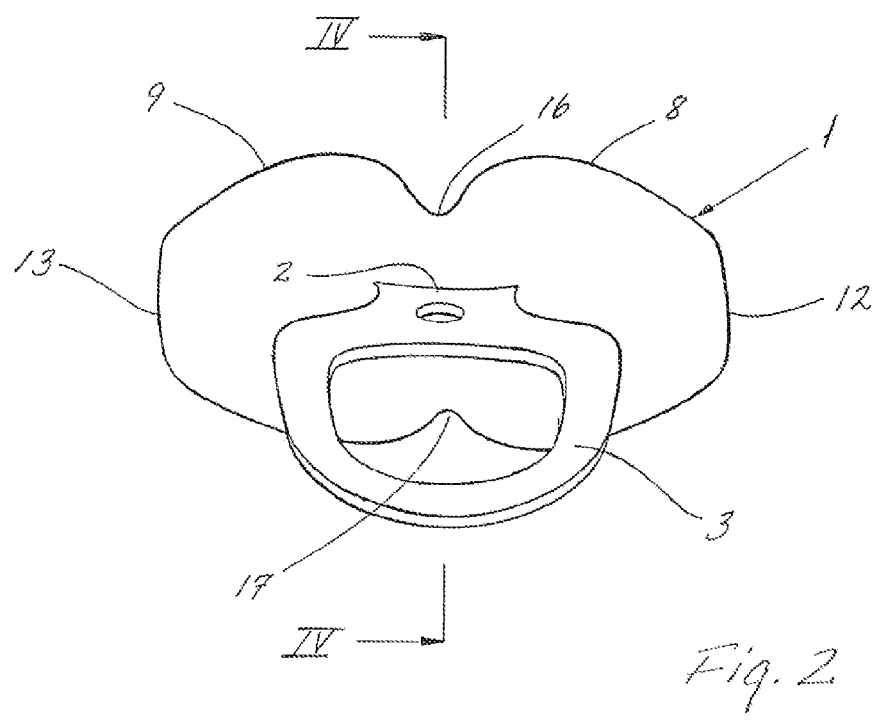
FIG. 2 is a front face view of the oral screen of FIG. 1.

With reference to the drawings, the lip and face muscles training device of the present invention comprises a screen 1 to which a pulling handle comprising a stem 2 and a grip 3 is attached in a central mid region of a front face 4 of the oral screen 1.

As illustrated in FIG. 4, the stem 2 extends in a horizontal plane L that intersects the oral screen and divides the same into an upper half 5 and lower half 6.

Basically, the upper and lower halves 5 and 6 are mirrored images of each other, but need not be perfectly identical. However, a substantially symmetrical design will permit a user to shift the device 180° in use, which may be desired in order to facilitate gripping about the stem by a less flexible hand, e.g.

Notably, for reasons discussed above, the stem 2 has a flat geometry wherein the horizontal width w of the stem transverse to its longitudinal extension is several times greater than its vertical height h. As a non-limiting advice to the skilled person the width w of the stem may be in the order of 10-15 mm, whereas the thickness or height h may amount to approximately 3 mm.

The grip 3, in the illustrated embodiment shaped as an eye, attaches to a free end of the stem 2 via a curved region R that directs the eye out of the longitudinal extension L of the stem 2. In the drawings the grip 3 is formed to point down below the plane of the stem, but may in other embodiments alternatively be pointing upwards above the plane of the stem.

Axially inside of the grip 3, as viewed in the longitudinal direction towards the screen 1, a lug 7 is formed as an opening in the stem 2. The lug 7 may be located in or near the curved region R and is adapted for attachment of a tension measuring instrument, or a tension load applying device (none of which is shown in the drawings).

Returning to the screen 1, the same is provided a composite curvature including a generally U-shaped horizontal projection (see FIG. 3) and a generally U-shaped or S-shaped vertical projection (see FIG. 4). More precisely, the left and right wings 8 and 9 of the screen extend curved in the longitudinal direction L sufficiently to reach beyond the premolar teeth on each side of the mouth of a user in applied position. To this purpose, the extension l of the screen in the longitudinal direction should at least amount to 30 mm in an oral screen intended for adult persons. In a children's oral screen, the same measure can be in the order of 22-25 mm, e.g.

As best seen in FIG. 4, the screen 1 has a curved cross-sectional profile and projection in the vertical plane, enclosing an intermediate angle a between the upper and lower halves of the screen. The intermediate angle a is the result of the upper and lower screen halves 5 and 6 diverging from a normal N to the horizontal plane L and to the stem 2, which attaches to the screen 1 at right angles to the normal N or, in other words, at a neutral angle with respect to the diverging upper and lower halves of the screen. In particular, the intermediate angle a may vary along the vertical extension of the screen. More precisely, on each side of the horizontal plane L, the curvature of the screen 1 in a vertical view may be composed of multiple intermediate angles a varying between an intermediate angle $a_{min}$ at a vertical mid region and an intermediate angle $a_{max}$ towards the upper and lower ends 10 and 11 of the vertical profile and projection of the screen. In the illustrated and preferred embodiment the varying intermediate angle forms a slightly S-shaped profile wherein $a_{min}$ corresponds to a deviation $d^+$ from the normal N in the order of 25-35°, whereas $a_{max}$ corresponds to a deviation $d^-$ from the normal N in the order of 15-25°. Thus on average the upper and lower halves 5 and 6 of the screen 1 enclose an intermediate angle a (max and min) of approximately 130°, although varying from about 120° at the central mid region to about 140° towards the upper and lower ends of the vertical profile and projection depicted in FIG. 4.

Notably however, the curvature applied to the screen as explained above reduces towards the rear ends 12 and 13 of the screen, which are generally flat if viewed in vertical sections near the ends 12 and 13.

The screen 1 and the stem 2 with the grip 3 are integrated into a one-piece element, such as a molded article produced in a suitable moldable material. All edges, in particular the edge running unbroken around the screen 1, are rounded and smooth and the average thickness of the entire device may be in the order of about 3 mm, approximately.

In the production of the lip and face muscles training device of the present invention, a texture is applied onto the front face 4 of the screen 1. The texture can be a regular or irregular pattern imprinted in the front face during molding, such as the ribbons, ridges or grooves 14 illustrated in FIG. 1. The texture can alternatively be a random pattern that is imprinted during molding or applied through abrasive blasting after molding, such as the coarse surface structure 15 illustrated in FIG. 3.

It will be realized that the texture applied to the front face of the screen enhances sensorimotor stimulation of the lips as the screen is pressed against the inside of lips under the tension load applied via the stem during use of the device. To the same purpose of enhanced stimulation, but through a maximized activation area, the screen is additionally designed to cover a vertical distance v between the upper and lower ends 10 and 11 of the vertical profile (see FIG. 4) amounting to about 30-35 mm in the adult version, and about 25 mm in the children's version of the device. In order to permit the screen to be sized as suggested, reliefs in form of generally V-shaped recesses 16 and 17 are formed in both upper and lower edges of the screen, respectively, to accommodate for the skin lugs or lip bands that connect the upper and lower lips to the adjacent gum.

From the above a skilled person will realize that modification of details are possible without departing from the scope and teachings of the invention as reflected in the claims and description.

The invention claimed is:

1. A device for training face, lip and throat muscles, the device comprising
    a rigid screen (1) configured to be inserted behind both upper and lower lips in a user's mouth, having a length between the screen ends (12, 13) configured to pass premolar teeth of the user in each side of the mouth when the screen (1) is applied,
    a pulling handle including a rigid stem (2) having a grip (3) attached to a front side (4) of the screen, operative for transfer of a tension load to the lips in use of the device,
    wherein the screen (1) is of compound curvature comprising generally U-shaped projections in both horizontal and vertical views respectively, the screen (1) in the vertical view having a convexo-concave sectional profile by which the screen (1), on a concave rear side of the screen, encloses an intermediate angle ($\alpha$) between upper (5) and lower (6) halves of the screen, the convexo-concave sectional profile gradually flattening towards the ends (12, 13) of the screen (1).

2. The lip and face muscles training device of claim 1, wherein the intermediate angle ($\alpha$) amounts to the order of 120-140° at a central region of the screen.

3. The lip and face muscles training device of claim 2, wherein the intermediate angle ($\alpha$) ranges from approximately 120° at a vertically mid region where the screen halves (5, 6) meet, to approximately 140° at upper and lower edges (10, 11) of the screen (1), in a slightly S-shaped sectional profile of the screen (1).

4. The lip and face muscles training device of claim 1, wherein a texture (14; 15) is applied onto the front side (4) of the screen.

5. The lip and face muscles training device of claim 4, wherein the texture is a regular or irregular coarse surface structure (15) molded into the front side, or applied through abrasive blasting.

6. The lip and face muscles training device of claim 1, wherein the stem (2) is a flat geometry with its major dimension (w) being horizontal.

7. The lip and face muscles training device of claim 1, wherein a grip (3) is attached in a free end of the stem (2), the grip angled out of a longitudinal direction (L) of the stem.

8. The lip and face muscles training device of claim 1, wherein a lug (7) for attachment of an instrument is formed in a region where the grip (3) attaches to the stem (2).

9. The lip and face muscles training device of claim 1, wherein an upper recess (16) and an opposite lower recess (17) is formed, respectively, in upper and lower edges of the screen (1).

10. The lip and face muscles training device of claim 2, wherein a texture (14; 15) is applied onto the front side (4) of the screen.

11. The lip and face muscles training device of claim 3, wherein a texture (14; 15) is applied onto the front side (4) of the screen.

12. The lip and face muscles training device of claim 10, wherein the texture is a regular or irregular coarse surface structure (15) molded into the front side, or applied through abrasive blasting.

13. The lip and face muscles training device of claim 11, wherein the texture is a regular or irregular coarse surface structure (15) molded into the front side, or applied through abrasive blasting.

14. The lip and face muscles training device of claim 6, wherein the stem (2) is a flat geometry with its major dimension (w) being horizontal.

15. The lip and face muscles training device of claim 2, wherein a grip (3) is attached in a free end of the stem (2), the grip angled out of a longitudinal direction (L) of the stem.

16. The lip and face muscles training device of claim 2, wherein an upper recess (16) and an opposite lower recess (17) is formed, respectively, in upper and lower edges of the screen (1).

\* \* \* \* \*